United States Patent [19]

Steude et al.

[11] Patent Number: 4,992,143
[45] Date of Patent: Feb. 12, 1991

[54] CONTINUOUS PROCESS FOR THE SEPARATION OF A PARTIALLY WATER SOLUBLE COMPONENT FROM A SLURRY

[75] Inventors: Heinrich E. Steude, Leverkusen, Fed. Rep. of Germany; Joerg Krell, McMurray; Charles F. Ho, Pittsburgh, both of Pa.; Charles E. Huffman, New Martinsville, W. Va.; Michael E. Bowsher, Crystal Lake, Ill.

[73] Assignee: Mobay Corporation, Pittsburgh, Pa.

[21] Appl. No.: 364,772

[22] Filed: Jun. 9, 1989

[51] Int. Cl.$^5$ ............................................. B01D 3/22
[52] U.S. Cl. ........................................ 203/26; 203/27; 203/96; 203/97; 203/98; 203/DIG. 8; 423/141
[58] Field of Search ...................... 203/26, 27, 98, 96, 203/97, DIG. 8; 202/158, 174; 423/141; 159/DIG. 8, DIG. 10, 24.2

[56] References Cited

U.S. PATENT DOCUMENTS

| | | | |
|---|---|---|---|
| 2,999,795 | 9/1961 | Yagi et al. | 203/10 |
| 3,326,266 | 6/1967 | Braithwaite et al. | 203/26 |
| 3,432,399 | 3/1969 | Schutt | 203/10 |
| 4,056,444 | 11/1977 | Weicht et al. | 203/26 |
| 4,145,228 | 3/1979 | Croce et al. | 106/304 |
| 4,161,429 | 7/1979 | Baiel et al. | 203/26 |
| 4,336,407 | 6/1982 | Smith, Jr. | 203/DIG. 6 |
| 4,783,242 | 11/1988 | Robbins | 202/204 |

OTHER PUBLICATIONS

Grant and Hackh's Chemical Dictionary, Fifth Edition (1987)—p. 541.

*Primary Examiner*—Virginia Manoharan
*Attorney, Agent, or Firm*—Joseph C. Gil; Lyndanne M. Whalen

[57] ABSTRACT

A continuous multistage process for separating a partially water soluble organic component from a slurry containing an insoluble solid, a partially water soluble organic component and optionally water. In this process, the slurry is continuously fed to a tower or column equipped with a suitable vapor/liquid contact device. Energy is applied at a point below the vapor/liquid contact device. Vapors containing the partially soluble organic component exit the tower or column overhead and the inorganic solid is recovered at the bottom of the tower or column. This application of distillation technology to slurries is particularly advantageous in that a more efficient separation of that solid material from the partially soluble organic component is obtained. The improved separation efficiency can be utilized to either lower separation cost and/or to affect a more complete separation in order to obtain a solid material with a lower residual amount of the organic component.

7 Claims, 3 Drawing Sheets

CONTINUOUS PROCESS FOR THE SEPARATION OF A PARTIALLY WATER SOLUBLE COMPONENT FROM A SLURRY

BACKGROUND OF THE INVENTION

The present invention relates to a continuous multistage distillation process for separating a partially water soluble component from a slurry containing an insoluble solid.

Such separation is required in the production of some inorganic pigments where the product pigment may be synthesized in the form of a slurry containing water and/or an organic compound, by-products and/or unreacted materials as well as the desired pigment. Recovery of the desired pigment in dry form requires removal of such organic compounds, by-products, and unreacted materials. The degree of difficulty in removing such materials necessarily depends upon the specific process and the particular materials present in the slurry.

An example of considerable economic relevance is the aniline process for manufacturing iron oxide color pigments. With a worldwide production capacity of 1.1 billion pounds per year, synthetic iron oxides are the largest volume color pigment in use. Concrete products, coatings and pigments for plastics are among the major markets.

Iron oxide color pigments are generally manufactured by one of four basic processes: (1) the Copperas process, (2) the precipitation process, (3) the Penniman process and (4) the aniline or so-called Bechamp process. In each of the first three processes, iron salts and, with the exception of the precipitation process, stamping scrap iron are used to generate iron oxides by roasting or by precipitation in an aqueous environment. Separation of the product iron oxide from its aqueous environment is readily accomplished.

In the aniline process (described e.g., in U.S. Pat. No. 4,145,228), however, mononitrobenzene is reacted with cast iron scrap in the presence of iron (II) and/or aluminum chloride solutions to produce both aniline and iron oxide. Separation of the crude aniline from the iron oxide is not as easily achieved as separation of iron oxide from water. In fact, such separation is commonly carried out in two stages. In the initial separation stage, crude aniline and a slurry in which iron oxide, water and by-products are present, are obtained from the reaction mixture. In a second step, the iron oxide is separated from the water and the inorganic by-products via conventional methods. Several methods for separation of the aniline from the slurry are known. Examples of such separation techniques are (1) vacuum distillation, (2) filtration, (3) steam distillation and (4) a combination of decantation and steam distillation.

Vacuum distillation of the reaction mixture generates a dry sludge having a very high residual aniline content. This residual aniline content can be reduced to an acceptable level only by subsequent distillation with live steam.

Filtration of the reaction mixture, e.g. through large metal screen filter boxes, yields an iron oxide-containing filter cake. This filter cake must then be washed with hot water or stripped with steam and dried. This separation technique has the disadvantage of reducing the quality of the iron oxide pigment and is difficult to control from an industrial hygiene viewpoint.

Steam distillation results in the most complete separation of aniline and iron oxide without detrimentally affecting the quality of the iron oxide pigment. In this separation method, live steam is introduced into the reactor in which the aniline and iron oxide are present to strip the volatile aniline from the reaction mixture. The resultant aniline-water distillate must then be decanted to separate the aniline and water layers. The aniline-containing water fraction and the aniline fraction must each be purified by additional distillation. The energy cost of such a distillation of the reaction mixture becomes prohibitive unless distillation is supplemented with a mechanical method of separation such as sedimentation.

Sedimentation may be accomplished by discontinuing the agitation of the reaction mixture after the reduction reaction has been completed. A thick slurry layer and a supernatant-aniline layer form very shortly after the agitation has stopped. The aniline layer may be readily siphoned off leaving a slurry made up of residual aniline, water, and iron oxide in the reactor. Live steam may then be introduced into the reactor and agitation of the mixture resumed. The steam distillation is continued until the aniline concentration in the mixture is reduced to approximately 500 to 1000 ppm. Reduction of the aniline content below this range is possible but not economically feasible because the cost of the steam required would far outweigh the benefits of product recovery and lower residual aniline content in downstream washing steps.

After distillation via live steam has been completed, the remaining crude iron oxide slurry is classified and washed to remove water soluble salts and foreign materials. The residue and the wash water from this treatment contain aniline and must therefore be processed, e.g. in a biological treatment facility, prior to disposal or recycling.

It would, therefore, be advantageous to improve the separation technology for such a mixture in a manner which would be more efficient and allow for a more complete separation than the known processes.

SUMMARY OF THE INVENTION

It is an object of the present invention to provide an economical and efficient process for separating a partially water soluble organic material from a slurry in which an insoluble solid is present without degrading the solid product.

It is also an object of the present invention to provide a separation process which is energy efficient, relatively uncomplicated and environmentally more desirable than prior art processes. The present invention makes it economically feasible to remove the organic material from the slurry to much lower residual levels than with prior art processes. The lower residual organic content will significantly reduce the environmental impact from the further processing of the slurry.

It is a further object of the present invention to provide a separation process in which the pressure drop of the gas phase in the distillation step is reduced to such an extent that energy recovery techniques which could not be used in prior art distillation processes may be employed.

Another object of the invention is to provide a separating system that does not become plugged due to solids settling, and further, does not carry over solids into the vapor stream.

These and other objects which will be apparent to those skilled in the art are accomplished by feeding a slurry containing an insoluble solid and a partially water soluble organic material into the top of a tower or column equipped with a vapor/liquid contact device and an energy source at the bottom. In a preferred embodiment of the invention, live steam is injected into the bottom of the tower or column. As the slurry passes through the tower or column, it is contacted with the vapor phase. The partially water soluble material vaporizes and exits the tower or column overhead. The solid containing slurry is recovered at the bottom of the column. The overhead vapors are condensed. The distillate is processed to recover the organic compound and a clean water phase.

DETAILED DESCRIPTION OF THE INVENTION

Any slurry containing an insoluble solid and an at least partially water soluble organic material may be separated on a continuous basis by the distillation process of the present invention. The present invention is particularly advantageous in the separation of slurries having a solids content from 5 to 65% by wt., preferably from 15 to 50% by wt., most preferably from 15 to 35% by wt.

The partially water soluble organic material present in the slurry to be separated may be any organic compound which is liquid at the temperature at which the slurry is to be separated and has a boiling point low enough that it will vaporize under the distillation conditions employed. Examples of such materials include solvents such as aniline or toluidine.

Any insoluble solid or mixture of insoluble solids which has a melting point above the distillation temperatures being used may be recovered with the slurry in accordance with the process of the present invention. Specific examples of appropriate inorganic solids include iron oxides and zinc oxides.

Water is often a component in slurries of the type which may be separated in accordance with the present invention. Where water is present in such a slurry, it will generally act as a partial solvent for the organic material.

Figure 1:
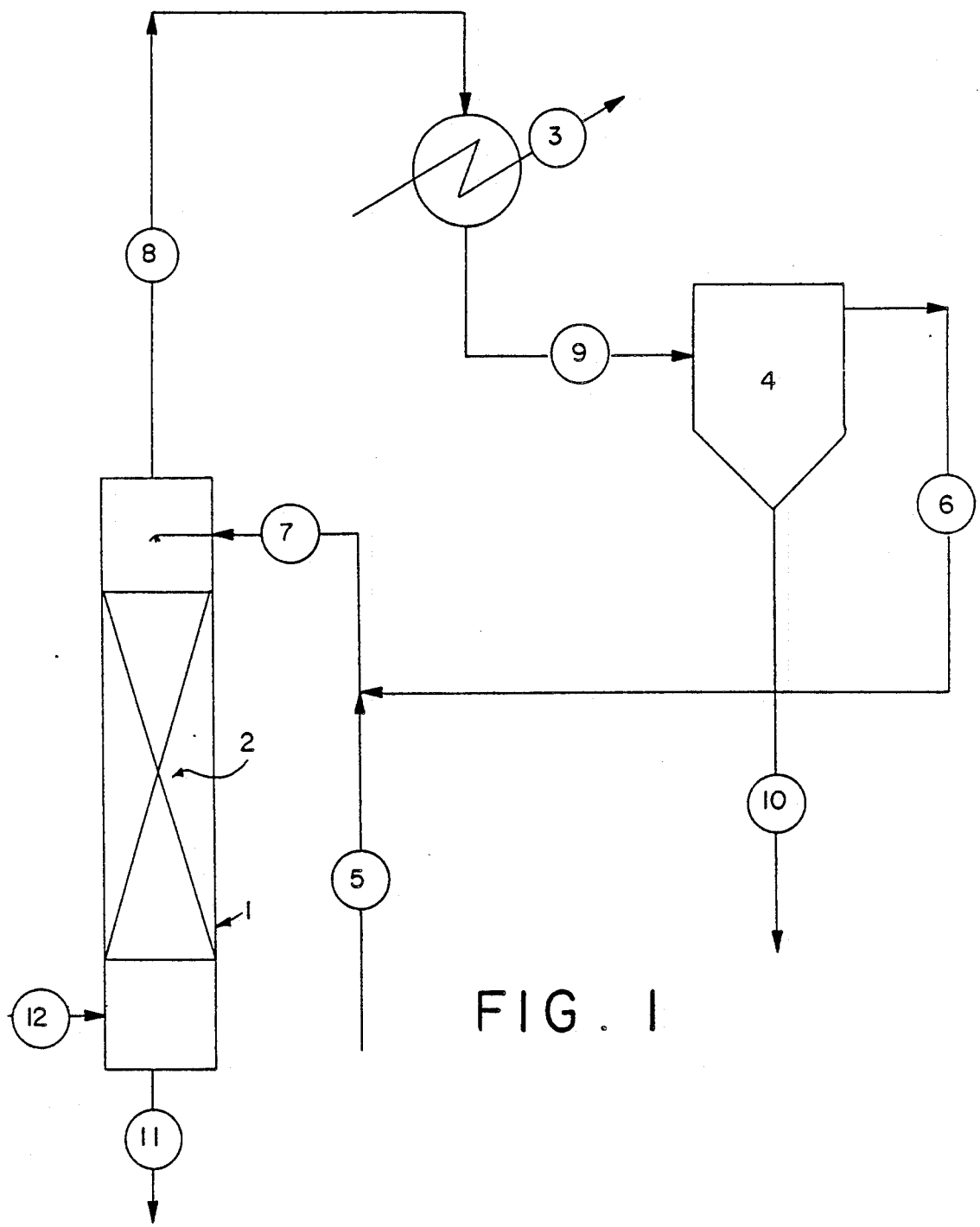
FIG. 1 illustrates an apparatus useful in carrying out the process of the present invention.
Figure 2:
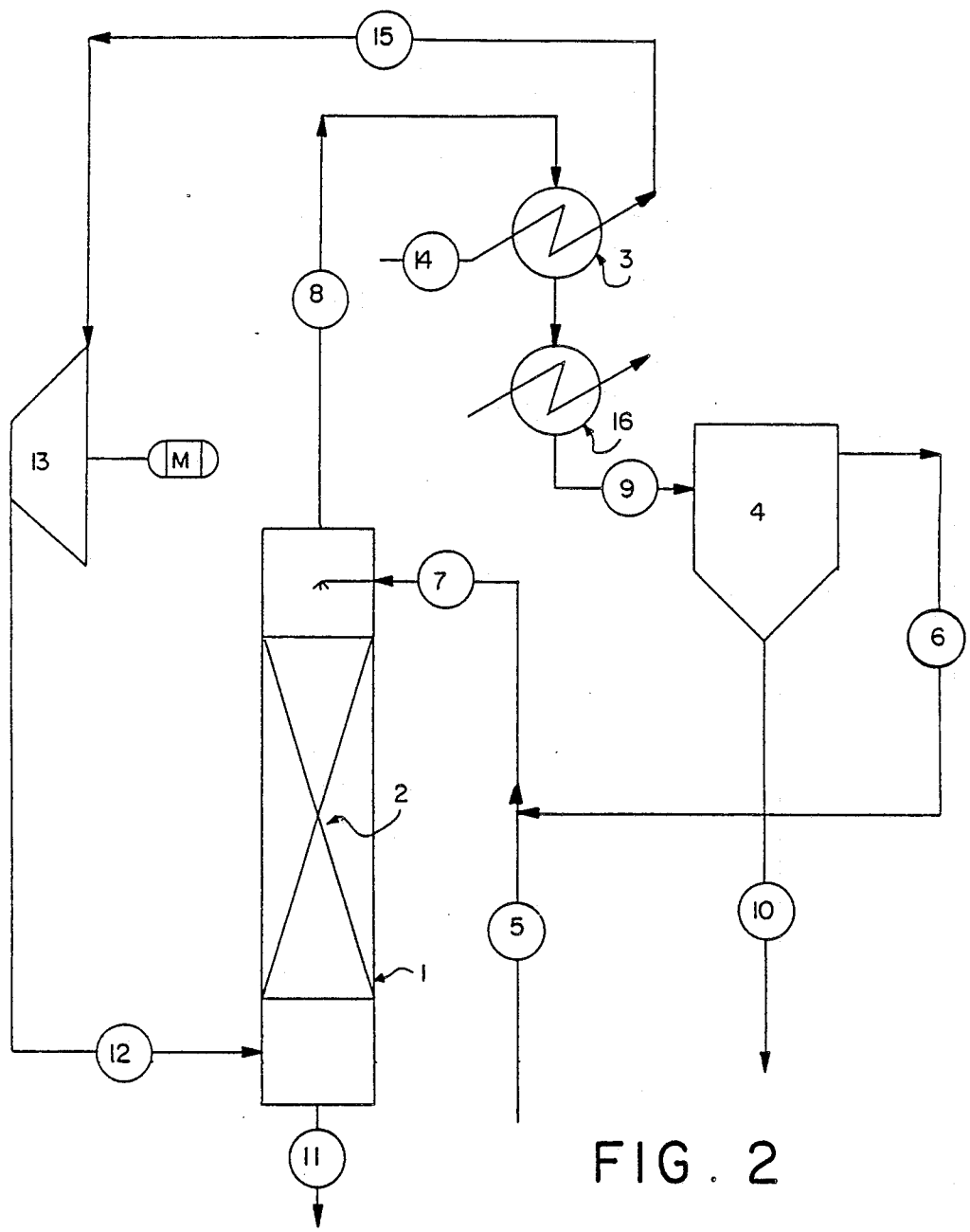
FIG. 2 illustrates a modification of the apparatus shown in FIG. 1 in which the heat from a vapor condenser is used to generate low pressure steam which steam is compressed and fed to the distillation column.

Although many slurries may be separated in accordance with the process of the present invention using a variety of apparatus, the present invention will be more specifically described in terms of a slurry made up of iron oxide, aniline and water and the apparatus schematically represented in FIGS. 1 and 2.

With reference to FIG. 1, the invention can be described as follows. The distillation tower 1 is filled with a single bed or multiple beds of packing 2. The slurry containing iron oxide, aniline, and water is fed into the distillation tower 1 via feed line 5 at a point 7 which may be above or below the top of the packing 2. Energy in the form of live or indirect steam is supplied to the tower 1 via injection line 12 at some point below the packing 2. The temperature of the iron oxide slurry and the live steam are substantially the same (i.e., the difference in temperature between slurry and steam is normally less than 10° C.). An aniline/water mixture exits the tower 1 via overhead line 8. This aniline/water mixture is then condensed and subcooled in condenser 3. The condensate is fed via line 9 into separation tank 4 where the condensate is separated into a water layer and an aniline layer. The separated aniline layer which is substantially aniline with the exception of dissolved water and other soluble impurities is recovered from separation tank 4 by means of recovery line 10. The aniline may be further separated and/or purified by conventional methods known in the art, if desired. The water layer containing aniline up to the solubility limit is removed from separation tank 4 through recovery line 6 and either sent to further processing and/or recycled into the iron oxide slurry feed line 5. This water may be used to dilute the slurry being fed to tower 1 to an appropriate solids content. Substantially aniline-free (i.e., less than 100 ppm, preferably less than 50 ppm aniline is present) iron oxide pigment and the majority of any water present in the slurry are recovered at the bottom of tower 1 via recovery line 11. The pigment may then be recovered in dry form by simple methods, e.g. filtration and drying.

It should be noted that while FIG. 1 illustrates a single bed packing, a multiple bed packing may also be employed. In fact, any suitable vapor/liquid contacting device (e.g. trays, grids, etc.) may be used instead of the single bed packing illustrated in FIG. 1. Packing materials useful in the present invention include grids made of ferritic stainless steel, carbon steel, Hastelloy B-2, Hastelloy C-276 and temperature and chemically resistant plastics.

It is readily apparent, however, that the contacting device employed must be suitable for handling slurries with substantial solids contents without plugging or build up while at the same time providing sufficient dispersion of the slurry phase to provide effective mass transfer between the "slurry" phase and the gas phase. An appropriate contacting device is selected on the basis of the rheological behavior of the specific slurry.

Figure 3:
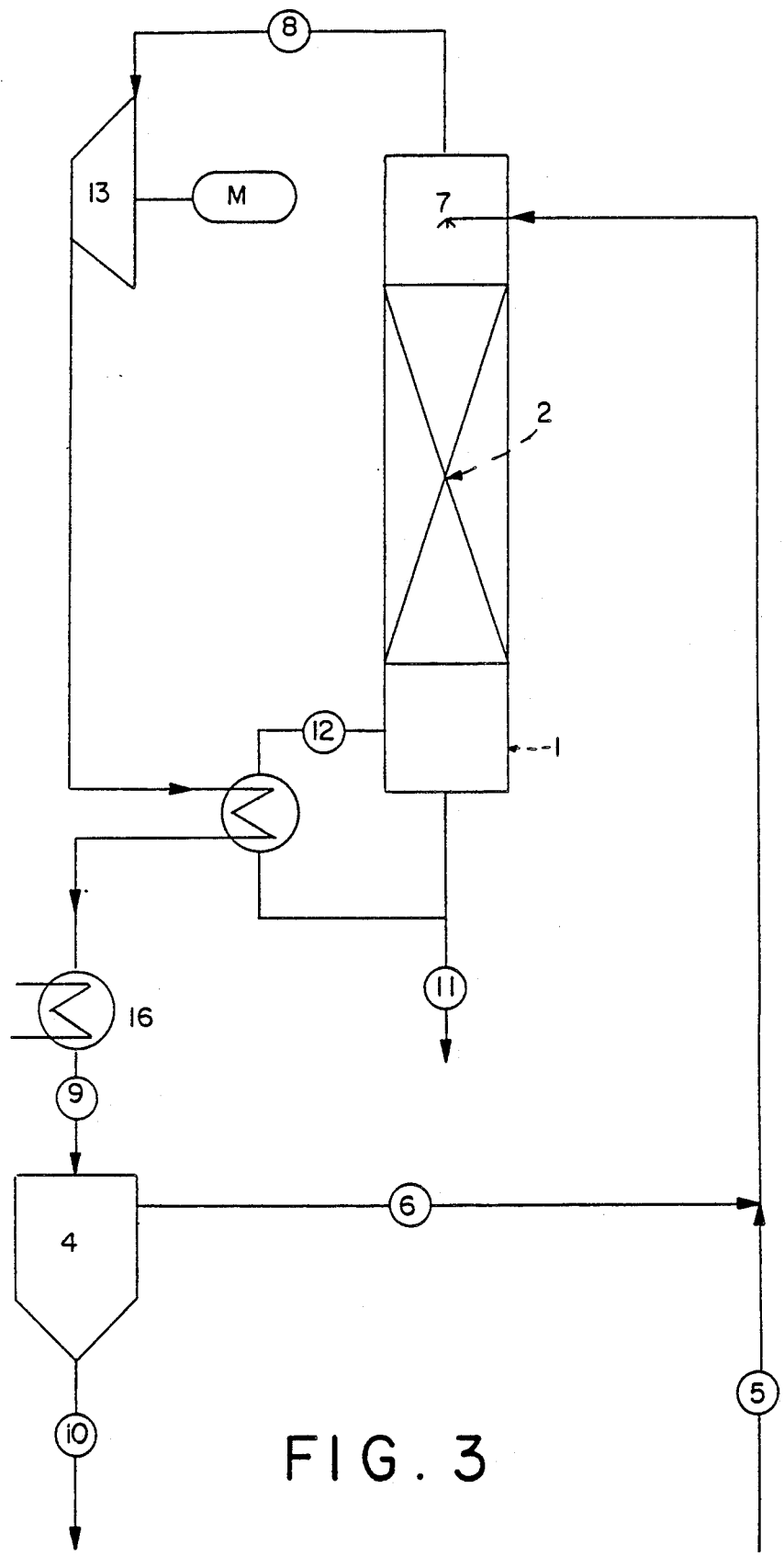
FIG. 3 illustrates an apparatus suitable for carrying out the process of the present invention in which the overhead vapors of the distillation column are pressurized and the heat of condensation is used as an energy source.

In the apparatus illustrated in FIGS. 1, 2, and 3 stacks of Glitsch Grid (a registered trademark of Glitsch Inc, Dallas, TX), which is an orderly, packing material with a well defined geometry were employed. This packing has a high open area to prevent pluggage, and its angled edges cause sufficient turbulence to promote intimate contact between the phases. The specific Glitsch Grid employed in the illustrated apparatus was composed of ferritic stainless steel. The present invention, however, is not limited to an apparatus in which this specific grid is employed.

Live steam is the energy source for the tower illustrated in FIG. 1. Any known energy source, however, may be used in the practice of the present invention. For example, a heat exchanger at the bottom of tower 1 would also be effective.

FIG. 2 illustrates a modification of the apparatus shown in FIG. 1 in which the heat from the overhead vapor exiting tower 1 by way of line 8 is used to evaporate water indirectly to generate low pressure steam. The aniline/water mixture is then cooled in cooler 16 before being fed into tank 4. The low pressure steam thus generated exits condenser/evaporator 3 by way of line 15 which feeds to compressor 13. The steam compressed in compressor 13 may then be fed via feed line 12 to tower 1.

In the apparatus illustrated in FIG. 3, the overhead vapors exiting tower 1 are fed to compressor 13 by way of line 8. Compression of these vapors in compressor 13 generates heat (heat of condensation) which heat is used as the energy source for tower 1. This heat is conveyed to the bottom of tower 1 by way of line 12.

It is readily apparent that any one of the apparatuses described above or a variation of any of these apparatuses permit the separation of the reaction mixture to be carried out on a continuous basis. In addition, the relative steam consumption per unit of aniline recovered is significantly lower in the process of the present invention where multiple stage distillation effects can be realized, than in the prior art steam distillation processes which are limited to a single stage distillation. This increase in separation efficiency makes it possible to use the same amount of steam in the present invention as was used in the prior art single stage steam distillation process to achieve an approximately tenfold decrease in residual aniline content.

The process of the present invention is also advantageous in that the slurry introduced as a continuous liquid phase into the tower or distillation column is converted to a distributed phase (i.e. is finely dispersed). The gas phase pressure drop is reduced to a level at which the indirect vapor recompression system illustrated in FIG. 2 becomes economically viable. This indirect vapor recompression system results in a further significant reduction of the energy necessary to accomplish a substantially complete separation of the slurry components. In fact, vapor recompression may reduce the overall energy input needed for separation by as much as 80%.

The iron oxide slurry recovered at the bottom of tower 1 has a residual aniline content of from 5 to 500 ppm, preferably less than 100 ppm and may be further purified, dried or roasted. The color quality and other physical properties of the iron oxide product are not affected by the separation process.

Having thus described our invention the following examples are given to illustrate that invention. All percentages given in these examples are percentages by weight, unless otherwise indicated.

EXAMPLES

In each of the following examples, a slurry of pigmentary grade iron oxide in water with aniline as the organic compound was used. Apparatus corresponding to that illustrated in FIG. 1 was used.

A slurry mixture containing between 15% and 40% solids and between 2% and 25% aniline was fed continuously from an agitated feed tank via feed line 5 to distillation tower 1. A feed pump, specifically a variable speed Moyno pump (manufactured by Robbins and Meyers Co. in Pittsburgh), pumped the slurry mixture to the top of the distillation tower 1 acting as multistage stripper. Prior to introduction of the slurry at feed point 7, the slurry was diluted with either fresh water or the aniline containing water phase recycled through line 6 from the tank 4 to the desired solids concentration. The solids concentration ranged between 15 and 35% and was adjusted to a value yielding a slurry viscosity optimal for the tower performance. The speed of the feed pump was adjusted to modulate the feed rate to achieve a suitable liquid loading of the packing.

The distillation tower 1 was filled with multiple beds of type EF 25A Glitsch Grid Packing 2 (a registered trademark of Glitsch Inc., Dallas, TX) as contacting device. For the small diameter tower, a feed distributor was not required. For a larger diameter tower, however, a distributor should be installed at the feed point. While the slurry was descending through the packing, the rising vapors stripped out the aniline. Several equilibrium stages were accomplished over the height of the packing. The slurry was continuously depleted of aniline which was transferred into the vapor phase.

The steam used for the stripping action was injected via feed line 12 under flow control into the bottom of the tower.

The slurry left the sump of the column continuously via line 11 at an aniline concentration of 5 to 100 ppm depending upon the steam to feed ratio and the initial aniline concentration, provided that a minimum steam to feed ratio of 6 lbs. of steam per pound of aniline removed was exceeded.

The overhead vapors containing the aniline removed from the slurry left distillation tower 1 via exit line 8. They were condensed in a water cooled condenser 3 and then sent via line 9 to a decanter tank 4 in order to separate them into a water-containing aniline phase (up to 8 wt.% water) which was removed via line 10 and an aniline-containing water phase (up to 5% aniline) which was removed via line 6. The water phase could be recycled to dilute the slurry feed stream. The aniline phase removed via line 10 was purified by dehydration and distillation to obtain commercial grade aniline.

In the experiments reported in Table 1, a 6" diameter column with a total packing height of 50 ft. was used. The feed rate varied between 1 gpm and 2 gpm resulting in a "liquid" loading of 5 to 10 gpm/ft$^2$ with 3 to 6% by weight aniline in the feed and a feed temperature of 90° C. A steam to aniline ratio of 6 to 7 lb. of steam per pound of aniline (at 30% solids, equivalent to 0.42 lb. steam per pound feed) was needed to strip to a residual aniline content of 50 ppm in the sump. The packing delivered about five theoretical stages. This separation efficiency compares favorably with the batch distillation in which, for the same starting conditions about 11 lb. of steam per pound of aniline were needed when stripping to 50 ppm. It was generally found that for the service conditions of the experiments, the packing performed at an HETP (height equivalent to a theoretical plate) of 8 to 12 ft.

By varying the steam rate at a constant slurry feed rate, the residual aniline content in the sump could be lowered to less than 10 ppm.

Under the conditions described above (liquid (slurry) loading=6 gpm/ft$^2$, steam rate=330 lb./h), the 50 ft. high packing induced a pressure drop ranging between 18 and 24 in. of water column. In a column equipped with an indirect vapor recompression system, the compressor would have to generate a compression ratio of about 1.30 where a mean temperature difference of 5° C. was realized in the condenser/evaporator to achieve a similar pressure drop range. The test column was operated with various iron oxide pigment grades. The column performance was remarkably stable against variations in pigment types, aniline concentration ranges, and liquid (slurry)-loadings as can be seen from the data presented in Table 1.

During the test runs, the parameters of which are reported in Table 1, samples were periodically taken from the feed stream, the bottoms stream and the decanter tank.

The feed sample was gravimetrically analyzed for solids concentration. The aniline content in the feed and bottoms sample was determined by analyzing an extract in a gas chromatograph. Since the iron oxide is a pigment, color evaluations were prepared using standard techniques. The results of these tests verified that the stripping process in the tower did not impair the quality of the iron oxide pigment.

TABLE 1

| SAMPLE | FEED RATE KG/HR | FEED TEMP | FEED WT PERCENT SOLIDS | FEED WT PERCENT ANILINE | SOLID-FREE PERCENT ANILINE | BOTTOMS SOLID-FREE ANILINE PPM | STEAM RATE KG/HR | STEAM ANILINE RATIO | ADJUST TO 90° C. FEED STM/ANILINE RATIO | ADJUST TO 90° C. FEED STM/FEED RATIO | LIQUID LOADING $M^3/HR/M^2$ | COLUMN SIMULATED THEOR. PLATES | OXIDE TYPE |
|---|---|---|---|---|---|---|---|---|---|---|---|---|---|
| Example A | | | | | | | | | | | | | |
| 1 | 562.95 | 33 | 21.1 | 3.18 | 4.03 | 6073 | 150.0 | 6.38 | 5.61 | 0.18 | 24.94 | 6− | A |
| 2 | 448.81 | 51 | 20.0 | 3.06 | 3.75 | 190 | 171.0 | 12.45 | 10.45 | 0.32 | 20.07 | 4− | A |
| 3 | 450.01 | 51 | 20.3 | 2.86 | 3.52 | 126 | 171.0 | 13.29 | 11.15 | 0.32 | 20.07 | 4+ | A |
| 4 | 463.20 | 53 | 23.8 | 2.33 | 2.99 | 34 | 171.0 | 15.84 | 13.44 | 0.31 | 20.07 | 5− | A |
| 5 | 419.44 | 52 | 20.1 | 2.10 | 2.75 | 16 | 171.0 | 19.41 | 16.57 | 0.35 | 18.74 | 5− | A |
| 6 | 422.23 | 52 | 20.9 | 2.40 | 2.96 | 14 | 171.0 | 16.87 | 14.41 | 0.35 | 18.74 | 5+ | A |
| 7 | 432.94 | 54 | 24.0 | 2.50 | 3.21 | 140 | 171.0 | 15.80 | 13.63 | 0.34 | 18.74 | 4− | A |
| Example B | | | | | | | | | | | | | |
| 1 | 515.06 | 45 | 39.8 | 6.50 | 10.79 | 22720 | 150.7 | 4.50 | 3.66 | 0.24 | 19.77 | 1+ | B |
| 2 | 351.31 | 59 | 31.2 | 5.52 | 8.02 | 48 | 149.4 | 7.70 | 6.94 | 0.38 | 14.39 | 5− | B |
| 3 | 351.32 | 59 | 31.0 | 5.64 | 8.17 | 44 | 149.4 | 7.54 | 6.79 | 0.38 | 14.39 | 5− | B |
| 4 | 345.90 | 59 | 28.9 | 5.23 | 7.36 | 28 | 149.4 | 8.26 | 7.43 | 0.39 | 14.39 | 5 | B |
| 5 | 295.01 | 55 | 31.0 | 5.66 | 8.20 | 28 | 149.4 | 8.95 | 8.11 | 0.46 | 12.08 | 5− | B |
| 6 | 294.97 | 55 | 31.0 | 5.82 | 8.43 | 7 | 149.4 | 8.70 | 7.88 | 0.46 | 12.08 | 5+ | B |
| 7 | 294.34 | 52 | 30.7 | 5.67 | 8.18 | 9 | 149.4 | 8.95 | 8.04 | 0.46 | 12.08 | 5+ | B |
| 8 | 294.95 | 56 | 31.0 | 5.54 | 8.03 | 6 | 149.4 | 9.14 | 8.31 | 0.46 | 12.08 | 5+ | B |
| 9 | 289.34 | 45 | 31.1 | 5.53 | 8.03 | 15 | 154.6 | 9.66 | 8.55 | 0.47 | 11.84 | 5− | B |
| 10 | 281.45 | 55 | 31.6 | 5.46 | 7.98 | 25 | 154.6 | 10.06 | 9.19 | 0.50 | 11.47 | 4.5 | B |
| 11 | 267.23 | 54 | 32.0 | 5.19 | 7.63 | 27 | 154.6 | 11.15 | 10.21 | 0.53 | 10.87 | 4+ | B |
| Example C | | | | | | | | | | | | | |
| 1 | 273.16 | 37 | 33.5 | 3.76 | 5.66 | 110 | 169.0 | 16.45 | 14.57 | 0.55 | 10.98 | 3+ | C |
| 2 | 285.59 | 36 | 32.5 | 4.20 | 6.22 | 73 | 169.0 | 14.09 | 12.35 | 0.52 | 11.56 | 3.5 | C |
| 3 | 288.12 | 34 | 33.7 | 4.40 | 6.64 | 69 | 169.0 | 13.33 | 11.64 | 0.51 | 11.56 | 4− | C |
| 4 | 294.19 | 35 | 29.9 | 3.90 | 5.57 | 56 | 181.0 | 15.78 | 13.81 | 0.54 | 12.15 | 4− | C |
| 5 | 277.27 | 33 | 28.7 | 2.60 | 3.64 | 44 | 181.0 | 25.11 | 21.97 | 0.57 | 11.56 | 3.5 | C |
| 6 | 268.62 | 34 | 31.3 | 3.40 | 4.95 | 49 | 181.0 | 19.82 | 17.55 | 0.60 | 10.98 | 3.5 | C |
| 7 | 283.65 | 33 | 26.5 | 4.00 | 5.44 | 30 | 193.0 | 17.01 | 14.94 | 0.60 | 12.03 | 4− | C |
| 8 | 274.61 | 34 | 27.4 | 3.00 | 4.13 | 29 | 193.0 | 23.43 | 20.73 | 0.62 | 11.56 | 4− | C |
| 9 | 271.85 | 33 | 26.1 | 3.90 | 5.28 | 26 | 193.0 | 16.20 | 16.07 | 0.63 | 11.56 | 4− | C |
| 10 | 335.92 | 30 | 24.4 | 2.90 | 3.83 | 27 | 193.0 | 19.81 | 16.71 | 0.48 | 14.49 | 4 | C |
| 11 | 333.31 | 29 | 23.4 | 3.20 | 4.18 | 22 | 193.0 | 16.10 | 15.22 | 0.49 | 14.49 | 4+ | C |
| 12 | 333.31 | 30 | 23.4 | 3.10 | 4.05 | 61 | 193.0 | 18.68 | 15.75 | 0.49 | 14.49 | 4− | C |
| 13 | 339.98 | 63 | 25.9 | 3.50 | 4.72 | 30 | 193.0 | 16.22 | 15.09 | 0.53 | 14.49 | 4− | C |
| 14 | 315.63 | 63 | 27.1 | 3.30 | 4.53 | 20 | 193.0 | 18.53 | 17.34 | 0.57 | 13.32 | 4− | C |
| 15 | 309.47 | 62 | 24.6 | 3.10 | 4.11 | 22 | 193.0 | 20.12 | 18.77 | 0.58 | 13.32 | 4− | C |
| 16 | 271.82 | 56 | 26.1 | 3.70 | 5.01 | 24 | 171.0 | 17.00 | 15.66 | 0.58 | 11.56 | 4− | C |
| 17 | 278.39 | 55 | 29.2 | 4.20 | 5.93 | 19 | 171.0 | 14.62 | 13.45 | 0.57 | 11.56 | 4 | C |
| 18 | 277.26 | 57 | 26.7 | 3.90 | 5.47 | 37 | 171.0 | 15.81 | 14.61 | 0.57 | 11.56 | 4− | C |
| Example D | | | | | | | | | | | | | |
| 1 | 308.83 | 55 | 15.5 | 3.20 | 3.79 | 94 | 140.1 | 14.18 | 12.38 | 0.40 | 14.34 | 4+ | D |
| 2 | 170.02 | 39 | 31.8 | 4.30 | 6.31 | 69 | 140.5 | 19.22 | 17.60 | 0.76 | 6.92 | 3− | D |
| 3 | 164.25 | 39 | 27.4 | 5.10 | 7.02 | 77 | 140.1 | 16.72 | 15.30 | 0.78 | 6.92 | 3− | D |
| 4 | 166.61 | 38 | 29.2 | 4.70 | 6.64 | 90 | 140.1 | 17.89 | 16.34 | 0.77 | 6.92 | 3− | D |
| 5 | 299.17 | 38 | 36.3 | 5.20 | 8.16 | 54 | 149.3 | 9.60 | 8.32 | 0.43 | 11.78 | 4+ | D |
| 6 | 301.46 | 44 | 37.3 | 5.60 | 8.94 | 76 | 149.3 | 8.84 | 7.81 | 0.44 | 11.78 | 4− | D |
| 7 | 260.07 | 45 | 38.1 | 5.40 | 8.72 | 75 | 156.5 | 11.14 | 10.10 | 0.55 | 10.10 | 3.5 | D |
| 8 | 250.93 | 42 | 33.3 | 5.80 | 8.69 | 97 | 158.0 | 10.86 | 9.76 | 0.57 | 10.10 | 3.5 | D |
| Example E | | | | | | | | | | | | | |
| 1 | 435.90 | 52 | 24.9 | 14.80 | 19.71 | 120211 | 114.6 | 1.78 | 1.42 | 0.21 | 18.72 | 1+ | E |
| 2 | 216.16 | 50 | 15.1 | 9.80 | 11.54 | 109 | 149.4 | 7.05 | 6.41 | 0.63 | 10.08 | 4− | E |
| 3 | 215.38 | 49 | 14.7 | 9.40 | 11.02 | 55 | 149.4 | 7.38 | 6.68 | 0.63 | 10.08 | 4+ | E |
| 4 | 204.58 | 52 | 11.7 | 6.90 | 7.81 | 18 | 145.4 | 10.58 | 9.67 | 0.67 | 9.83 | 4.5 | E |
| 5 | 89.58 | 39 | 20.6 | 12.10 | 15.23 | 19 | 150.2 | 13.86 | 13.24 | 1.60 | 3.99 | 3+ | E |
| 6 | 89.91 | 33 | 21.0 | 13.40 | 16.96 | 25 | 149.4 | 12.40 | 11.76 | 1.58 | 3.99 | 3+ | E |
| 7 | 138.39 | 39 | 30.2 | 17.65 | 25.28 | 24 | 154.6 | 6.33 | 5.97 | 1.05 | 5.70 | 4− | E |
| 8 | 138.01 | 47 | 29.6 | 18.20 | 25.94 | 41 | 156.3 | 6.22 | 5.92 | 1.08 | 5.70 | 4− | E |
| 9 | 139.09 | 46 | 30.6 | 18.20 | 26.32 | 20 | 156.3 | 6.17 | 5.87 | 1.07 | 5.70 | 4− | E |
| 10 | 138.62 | 43 | 30.4 | 14.90 | 21.41 | 39 | 156.3 | 7.57 | 7.16 | 1.07 | 5.70 | 4− | E |
| 11 | 138.00 | 41 | 29.8 | 17.50 | 24.93 | 24 | 156.3 | 6.47 | 6.12 | 1.07 | 5.70 | 4− | E |
| 12 | 138.26 | 46 | 30.1 | 17.90 | 25.59 | 24 | 156.3 | 6.32 | 6.01 | 1.08 | 5.70 | 4− | E |
| 13 | 138.27 | 42 | 30.1 | 16.70 | 23.88 | 20 | 158.1 | 6.85 | 6.46 | 1.08 | 5.70 | 4− | E |
| 14 | 137.21 | 41 | 29.1 | 17.50 | 24.67 | 41 | 158.1 | 6.58 | 6.23 | 1.09 | 5.70 | 4− | E |

TABLE 1-continued

| SAMPLE | FEED RATE KG/HR | FEED TEMP | WT PER-CENT SOL-IDS | WT PER-CENT ANI-LINE | SOLID-FREE PER-CENT ANI-LINE | BOT-TOMS SOLID-FREE ANILINE PPM | STEAM RATE KG/HR | STEAM ANI-LINE RATIO | ADJUST TO 90° C. FEED STM/ANI-LINE RATIO | ADJUST TO 90° C. FEED STM/FEED RATIO | LIQUID LOADING M³/HR/M² | COLUMN SIMULATED THEOR. PLATES | OXIDE TYPE |
|---|---|---|---|---|---|---|---|---|---|---|---|---|---|
| 15 | 137.08 | 42 | 29.0 | 16.70 | 23.50 | 33 | 166.7 | 7.28 | 6.91 | 1.15 | 5.70 | 4— | E |
| 16 | 135.74 | 42 | 27.7 | 17.80 | 24.62 | 13 | 166.7 | 6.90 | 6.55 | 1.17 | 5.70 | 4— | E |

A = Yellow
B = Blueish black
C = Medium shade red
D = Light shade red
E = Medium shade red with recycle material from the aniline purification area Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous multistage distillation process for separating a partially water soluble organic component from a slurry containing 5% by weight to 65% by weight of an insoluble solid, up to 95% by weight of the partially water soluble organic component and optionally water comprising (a) feeding the slurry to a tower or column equipped with a contact device capable of handling suspensions with substantial solids contents at a point above or below the contact device, (b) applying heat supplied by steam at a point below the contact device, (c) condensing the vapors containing the partially water soluble component which exit the tower or column overhead, (d) recovering the slurry containing the insoluble solid at the bottom of the tower or column and (e) repeating steps (a), (b), (c) and (d) so that the need to interrupt the distillation to allow sedimentation of the insoluble solid is avoided.

2. The process of claim 1 in which the inorganic solid is an iron oxide pigment and the partially water soluble component is aniline.

3. The process of claim 1 in which the contacting device is a single or multiple bed packing.

4. The process of claim 1 in which the contacting device is at least one tray.

5. The process of claim 1 in which the heat released during condensation of the overhead vapors is used to generate steam which steam is pressurized with a compressor and used to supply heat for the continuous multistage distillation.

6. The process of claim 1 in which the contact device is a stack of grids.

7. The process of claim 1 in which the heat generated during (c) supplies the heat for (b).

* * * * *